United States Patent [19]

Salmon et al.

[11] 4,057,618

[45] Nov. 8, 1977

[54] RADIOIODINATED BLEOMYCIN

[75] Inventors: Sydney E. Salmon; Rosa H. Liu, both of Tucson, Ariz.

[73] Assignee: University Patents, Inc., Stamford, Conn.

[21] Appl. No.: 682,150

[22] Filed: Apr. 30, 1976

[51] Int. Cl.$^2$ .................... A61K 29/00; A61K 43/00
[52] U.S. Cl. ............................................ 424/1; 424/9
[58] Field of Search .................. 424/1, 1.5, 9, 114, 424/180, 181; 260/210 AB

[56] References Cited

U.S. PATENT DOCUMENTS 3,957,963   5/1976   Salmon et al. ........................... 424/1

FOREIGN PATENT DOCUMENTS 2,134,653   4/1972   France ..................................... 424/1
2,199,455   9/1972   France ..................................... 424/1

OTHER PUBLICATIONS

Bolton et al., Nuclear Science Abstracts, vol. 28, No. 8, Oct. 31, 1973, p. 1696, Abstract #17978.

*Primary Examiner*—Benjamin R. Padgett
*Assistant Examiner*—Christine M. Nucker
*Attorney, Agent, or Firm*—Mason, Kolehmainen, Rathburn & Wyss

[57] ABSTRACT

Radioiodinated bleomycin is a useful imaging agent for body tissues. Its production by reaction of bleomycin with N-hydroxysuccinimide esters of radioiodinated hydroxyphenylalkanoic acid is described.

7 Claims, No Drawings

RADIOIODINATED BLEOMYCIN

This invention relates to radioiodinated hydroxyphenylacyl bleomycin and methods for its production.

BACKGROUND OF THE INVENTION

In recent years much attention has been directed toward the development of radiopharmaceuticals that will concentrate in tumor tissue and permit external imaging of the tumor. Such an approach, if completely successful, would have obvious advantages over other methods currently employed for staging and followup of patients with malignant disease because of the inherent simplicity, lower cost, and low morbidity of scanning techniques. Although an ideal tumor imaging agent has not yet come into routine clinical use, the chance observation that the radionuclide gallium—7 citrate accumulated in soft tissue tumors has led to extensive clinical experience with this particular tumor scanning agent.

Another more rational approach to tumor imaging is to label tumor-specific drugs or antibodies which might selectively concentrate in tumors. The anti-tumor antibiotic bleomycin is such a drug and it has been shown to concentrate in skin, lung, and certain tumors. It has recently been approved for general use on the basis of its demonstrated clinical effectiveness against squamous cell carcinomas, lymphoma, and testicular tumors.

Bleomycin has the desirable characteristic of chelation with a number of bivalent and trivalent cations, such as cobalt, lead, indium and copper. It has thus been possible to chelate radioactive isotopes of such metals to bleomycin and thereby produce radioactive agents which can be used to detect and visualize tumors.

Bleomycin is a mixture of glycopeptide antibiotics discovered by Umezawa et al in 1962, and isolated from the cultured broth of *Streptomyces verticillus*. It is effective against various animal and human tumors such as squamous cell carcinomas, malignant lymphomas, and testicular tumors. The antibiotic also inhibits the growth of gram positive and gram negative bacteria and appears to bind to cellular DNA.

Thirteen distinct, but closely related, bleomycin peptides have been isolated. They are relatively high molecular weight (ca. 1200), and are known to form metal chelates, as well as being concentrated in tumors.

Bleomycin can be loosely chelated with a wide variety of radionuclides including indium 111, cobalt 57 and lead 203. Studies have been conducted of $^{111}$In-labeled bleomycin as a tumor-imaging agent in patients with a wide variety of neoplasms. The precise mechanism of tumor labeling with $^{111}$In-bleomycin is not fully understood. Although $^{111}$In alone will localize tumors to some extent, the results indicate that tumor localization occurs more frequently with $^{111}$In-labeled bleomycin. However, the radionuclide ($^{111}$In) can dissociate from bleomycin; serum transferrin and the erythroid compartment of the bone marrow both compete with bleomycin for $^{111}$In binding. Ionic indium released by bleomycin on dissociation is bound virtually quantitatively to transferrin and accumulated by bone marrow erythroid precursor cells.

A broad spectrum of tumors can be localized with radioactive-labeled bleomycin, despite the lack of therapeutic efficacy of bleomycin alone against these tumors. It appears that two essential steps are involved at the cellular level for bleomycin to exert its oncolytic effect: (a) selective uptake by tumor cells and (b) specific inhibition of DNA synthesis and cell death due to bleomycin's antibiotic effect. Thus, bleomycin can serve as a vehicle for delivering local radioactivity to the traget tumor tissue.

$^{111}$In-bloemycin is an important tumor-scanning agent, but it has certain disadvantages. For instance, bleomycin is known to concentrate in the lung and it is possible that diffuse pulmonary uptake of $^{111}$In-bleomycin identifies either those patients with pulmonary damage or those who are susceptible to subsequent development of bleomycin pulmonary toxicity. Another disadvantage is that the $^{111}$In-bleomycin dissociates in body fluids and releases $^{111}$In ions which are absorbed by normal liver and bone marrow which are thereby imaged. Apparently $^{111}$In dissociated from $^{111}$In-bleomycin competes with iron for binding to transferrin and for incorporation into erythroid precursors in the bone marrow.

A tumor-imaging agent should have the following properties: (a) it should be taken up by all malignant tissue in the patient (i.e., highly sensitive); (b) it should not be taken up by any normal or nonmalignant tissues (i.e., highly specific); (c) it should be safe to administer and not give an excessive radiation dose (so that it may be easily and safely employed for serial evaluations); and (d) it should be capable of providing good images with currently available instrumentation (so that only the intrinsic resolution of the instrument would limit the size of the minimally detectable lesion). While clinical data indicate that $^{111}$In-bleomycin is a safe and clinically useful tumor-imaging agent, it is not ideal by these criteria, although it does represent an advance in efforts to develop the ideal radiopharmaceutical.

Lesion detectability is dependent upon two factors: (a) absolute uptake of the agent in question by the tumor and (b) the contrast between the activity present in the tumor and that in adjacent normal tissues. While $^{111}$In-bleomycin is effective in certain areas, there is still need for radioactive scanning agents which are more stable than chelated materials such as $^{111}$In-bleomycin and which are more selective in tissue uptake.

OBJECTS OF THE INVENTION

It is an object of this invention to provide radioactive compounds of bleomycin which are more stable than $^{111}$In-bleomycin complexes.

Another object is to provide methods of producing radioiodine-bleomycin compounds.

An additional object is to provide radioiodinated bleomycin imaging agents for body tissues.

A further object of this invention is to provide radioiodine-labeled bleomycin compounds which in large doses can function as tumor-seeking radiochemotherapeutic anticancer drugs.

Another object is to provide radioiodinated hydroxyphenylalkanoyl bleomycin and a method for the production thereof.

GENERAL DESCRIPTION OF THE INVENTION

We have discovered that bleomycin labeled with radioactive iodinated hydroxyphenylalkanoyl substituents is more stable than $^{111}$In-labeled bleomycin. The radioiodine is attached to the hydroxyphenylalkanoyl radical which is conjugated with one or more amino groups of bleomycin and does not dissociate in aqueous fluids as do metal ions which are chelated to the bleomycin molecule, such as copper, cobalt and indium.

We have also discovered that radioiodinated hydroxyphenylalkanoyl bleomycin is attracted to tumor tissue in animals and humans and in this way delivers a highly radioactive isotope, radioiodine, specifically to such tissue. It thus serves as a scanning agent for imaging and locating tumor tissue in the body.

We have further discovered procedures for producing radioiodinated hydroxyphenylalkanoyl bleomycin which are not destructive of the bleomycin and do not interfere with its antibiotic activity.

The location of radioiodinated hydroxyphenylalkanoyl bleomycin in the body can be determined by scanning with a dual-probe rectilinear scanner, a multi-channel analyzer, a gamma camera, or scintillation camera. By this procedure the tissue in which the radioiodinated bleomycin has localized can be visulaized and identified.

The radioactive isotopes of iodine used in preparing the radioiodinated hydroxyphenylalkanoyl bleomycin have relatively short half lives (13.3 hours to 60 days) in contrast to radioactive cobalt (270 days). These shorter half lives avoid the disadvantages of routine collection and storage of urine of patients for the first 2 days after administration.

The radioiodinated hydroxyphenylalkanoyl substituent is represented by the following formula:

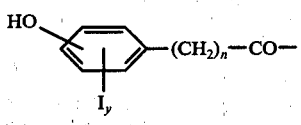

wherein $n$ is an integer from 1 to 4, inclusive, and $y$ is a number from 0.5 to 2, inclusive. The number of such substituents per bleomycin molecule can vary from 0.5 to 3. The preferred radioiodinated hydroxyphenylalkanoyl substituent is the radioiodinated p-hydroxyphenylpropionyl substituent, derived from radioiodinated p-hydroxyphenylpropionic acid ester of N-hydroxysuccinimide, which is known as the Bolton-Hunter reagent (Biochem. J. 133, 529–539 (1973). Similar radioodinated reagents are produced by radioiodinating N-hydroxysuccinimide p-hydroxyphenylacetate and p-hydroxyphenylbutyrate.

The N-hydroxysuccinimide esters of radioiodinated hydroxyphenylalkanoates react with the primary amino groups of bleomycin to introduce radioiodinated hydroxphenylalkanoyl groups on the amino groups of the bleomycin molecule, thus producing radioiodinated hydroxyphenylalkanoamide bleomycin compounds. The latter are generically described herein as radioiodinated hydroxyphenylalkanoyl bleomycin.

In accordance with our invention, bleomycin in a buffer solution at neutral or slightly alkaline pH is reacted at low temperature with an iodinated hydroxyphenylalkanoic acid ester of N-hydroxysuccinimide, wherein the I is $I^{123}$, $I^{125}$ or $I^{131}$, in an alkaline medium, which acylates the amino groups of the bleomycin. After the reaction the excess of radioactive iodine is removed, preferably with ion-exchange glass beads or an ion-exchange gel resin which absorbs ions or iodinated small molecules but not the radioiodinated bleomycin. The latter can be used in the aqueous solution in which it is isolated, or can be separated therefrom and purified by known techniques used for the isolation and purification of bleomycin.

The amount of raiodiodine introduced into the bleomycin can vary substantially. The amount need only be sufficient for scanning with available instruments. The practical range is 0.1 to 5 millicuries of radioiodine per milligram of bleomycin. In practice 1–3 millicuries/mg is desirable; this level is adequate for both diagnostic and therapeutic use of idobleomycin. $^{125}$I-bleomycin is stable for at least 1 month. $^{123}$I-bleomycin has excellent imaging properties and a short half-life (13.3 hours).

The dosage level of the radioiodinated bleomycin is less than 0.5 milligram per square meter of body surface area, usually 0.2 to 0.3 mg per m$^2$, although dosages up to 15 mg/m$^2$ can be administered. Three isotopes of iodine ($I^{123}$, $I^{125}$ and $I^{131}$) can be utilized for labeling of bleomycin through iodinated hydroxyphenylalkanoyl substituents. $I^{125}$ has a long (60-day) half-life and is preferred for long shelf life, whereas $I^{123}$ and $I^{131}$ have shorter half-lives which are valuable in external scanning.

When iodination is performed with an acylating agent such as the Bolton-Hunter reagent ($^{125}$I) the radioiodination of bleomycin is conducted in aqueous solution at pH of about 6.5–8.5, preferably in a buffered solution at low temperature in the range of 0°. The radioiodine is supplied as one of the following radioiodide ions: $^{123}I^-$, $^{125}I^{31}$, or $^{131}I^-$. The reaction mixture can be passed through ion-exchange resin or gel to remove radioiodide ions and other anions or cations to produce an aqueous solution of radioiodinated bleomycin suitable for parenteral administration.

EXAMPLE 1

Bleomycin was subjected to iodination with the Bolton-Hunter reagent ($^{125}$I) which is the N-hydroxysuccinimide ester of iodinated-p-hydroxyphenylpropionic acid. The active ester acylates terminal amino groups with the iodinated-p-hydroxyphenylpropionic residue. A reaction vial containing 2.0 mCi (500 Ci/mM) of the Bolton-Hunter reagent was chilled to 0° C and kept on ice in a chemical hood. Bleomycin was dissolved in 0.1 M pH 8.5 borate buffer solution with a final bleomycin concentration of 0.5 mg per ml, and 3.0 microliters of the bleomycin solution (containing 1.5 micrograms of bleomycin) was added to the reaction vial and the mixture agitated for 45 minutes at 0° C. Then 0.5 ml of 0.2 M glycine in 0.1 M borate buffer (pH 8.5) was added and the reaction vial was shaken for an additional 5 minutes and then transferred to a gel chromatographic column (Sephadex G-25 fine grade, bed volume 40 ml) and eluted with 0.02 M citrate saline buffer (pH 7.5). By this procedure, an aqueous solution of $^{125}$I-bleomycin was produced, which, after sterilization, was suitable for administration to humans and animals. Column monitoring was carried out both measurements of absorbency of bleomycin at 280 anometers and by radioactivity counting with an automatic gamma counter. The specific activity of the product was 2–4 mci/mg of bleomycin.

EXAMPLE 2

This example illustrates uptake of $^{125}$I-bleomycin by mouse tumor cell. 70–80 mg of $^{125}$I-bleomycin labeled with Bolton-Hunter reagent was added in vitro to each of a series of tubes containing 5 million Ridgway osteogenic sarcoma cells. This form of cancer of inbred mice is sensitive to bleomycin treatment. At hourly intervals cells were harvested and washed free of unincorporated $^{125}$I-bleomycin and the cells collected for radioactivity counting for determination of $^{125}$I-bleomycin contents.

At end of 5 hours incubation, there was an active uptake of bleomycin $I^{125}$ by tumor cells. The range was between 1.8 mg and 1.25 mg per 5 million cells, that is $1.4 \times 10^5$ to $1.0 \times 10^5$ molecules of bleomycin $I^{125}$ entered one cell after 5 hours reaction time.

EXAMPLE 3

The following data show quantititative uptake of radioiodinated bleomycin by Ridgway osteogenic sarcoma cells from five different experiments. The numerical values in the table represent the cpm measured for the time interval divided by the cpm at time zero. In each case the increase in uptake of the radioiodinated bleomycin is clear-cut. The highest uptakes are in the range of two times the concentration of radioactivity present at time zero. They may represent far more than a twofold drug uptake because of the problems of background subtracting of radioactivity which cannot necessarily be completely washed from the cells. The data indicate that there the radioiodinated bleomycin is effectively absorbed by tumor cells.

| Experiment Time | $I^{125}$ Bleomycin | | | | |
|---|---|---|---|---|---|
| | A | B | C | D | E |
| 30 min. | 1.33 | 1.08 | 1.1 | 1.13 | 1.55 |
| 60 min. | 1.27 | 1.09 | — | 1.13 | 1.86 |
| 2 hrs. | 1.53 | 1.13 | 1.80 | 1.45 | 1.77 |
| 3 hrs. | 2.12 | 1.18 | 1.87 | 1.54 | 1.94 |
| 5 hrs. | | 1.32 | 1.83 | 1.60 | 2.00 |

We claim:
1. Radioiodinated hydroxyphenylacyl bleomycin, wherein the radioiodine is selected from the group consisting of $I^{123}$, $I^{125}$ and $I^{131}$.
2. Radioiodinated hydroxyphenylacyl bleomycin as defined by claim 1, wherein the radioiodinated bleomycin contains about 0.1 to about 5 millicuries of radioiodine per milligram of bleomycin.
3. Method for producing radioiodinated bleomycin which comprises reacting bleomycin in aqueous solution with radioiodinated hydroxyphenylacyl N-hydroxysuccinimide then separating the radioiodinated hydroxyphenylacyl bleomycin from the excess of radioiodide ion to produce an aqueous solution of radioiodinated bleomycin.
4. Method of claim 3 wherein the radioiodide ion is selected from the group consisting of $^{123}I^-$, $^{125}I^-$ and $^{131}I^-$.
5. Method of claim 4 wherein the aqueous solution of bleomycin is maintained at a pH of 6.5 to 8.5.
6. Method of claim 5 wherein the hydroxyphenylacyl radical is p-hydroxyphenylpropionyl.
7. Method of claim 5 wherein the excess of radioiodide ion is removed by ion exchange or gel permeation chromatography.

* * * * *